United States Patent
Allah et al.

(10) Patent No.: US 7,282,227 B2
(45) Date of Patent: Oct. 16, 2007

(54) **METHOD FOR TREATING HEPATITIS C WITH EVAPORATE OF *ECBALLIUM ELATERIUM* EXTRACT**

(75) Inventors: Essam M. A. Hob Allah, Cairo (EG); Said I. A. Shalaby, Cairo (EG)

(73) Assignee: Kentara Research LLC, Kitty Hawk, NC (US)

( * ) Notice: Subject to any disclaimer, the term of this patent is extended or adjusted under 35 U.S.C. 154(b) by 0 days.

(21) Appl. No.: 10/637,684

(22) Filed: Aug. 8, 2003

(65) Prior Publication Data

US 2004/0142051 A1    Jul. 22, 2004

Related U.S. Application Data

(60) Provisional application No. 60/402,373, filed on Aug. 9, 2002.

(51) Int. Cl.
*A61K 36/00* (2006.01)
(52) U.S. Cl. .................. 424/777; 424/725
(58) Field of Classification Search ........ 424/725, 424/195.1, 774, 777
See application file for complete search history.

(56) References Cited

U.S. PATENT DOCUMENTS

| | | | |
|---|---|---|---|
| 5,089,474 A | 2/1992 | Castro et al. | |
| 5,118,673 A | 6/1992 | Carpenter | |
| 5,648,089 A | 7/1997 | Shawkat | |
| 5,763,430 A | 6/1998 | Zasloff | |
| 5,874,804 A | 2/1999 | Rogers | |
| 5,876,728 A | 3/1999 | Kass et al. | |
| 6,841,174 B2 | 1/2005 | Shalaby et al. | |
| 2004/0142052 A1 | 7/2004 | Allah et al. | |

FOREIGN PATENT DOCUMENTS

EP    0 793 964 B1    12/1998

OTHER PUBLICATIONS

Mylonakis et al. Plasma Viral Load Testing in the Management of HIV Infection; American Family Physician; Feb. 2001 pp. 1-7.*
HIV/AIDS Monitoring; Improved Viral Load Test Approved by FDA; Blood Weekly; Atlanta; Sep. 2002 pp. 1-2.*
Animal Models (HBV0; Trimera Disease Model Developed for Hepatitis B; Cancerweekly Plus; Atlanta; Feb. 1999 pp. 1-2.*
Davis, G. Treatment of Chronic Hepatitis C; British Medical Journal; Nov. 2001 pp. 1-3.*
The New England Journal of Medicine, vol. 339, No. 21, Nov. 19, 1998, pp. 1485-1492.
David M.R. Culbreth; A Manual of Materia Medica and Pharmocology, 1927, two pages.
Harvey Wickes Feltzer and John Uri Lloyd, *King's American Dispensatory*, 1898 (5 pages).
Robert T. Gunther, *The Greek Herbal at Discorides*, New York Hafner Press, 1934, p. 547.
E. Yesilada, S. Tanaka, E. Sezik and M. Tabata, "Isolation of an anti-inflammatory principle from the fruit juice of *Ecballium elaterium*", *J. Nat. Prod.*, May-Jun. 1998, 51(3), p. 504.
A. Favel, H. Mattras, M.A. Coletti-Previero, R. Zwilling, E.A. Robinson and B. Castro, "Protease Inhibitors from *Ecballium elaterium* Seeds," *Int. J. Peptide Protein Res.*, 33, (1989), pp. 202-208.
J. Remington et al., editors, *The Dispensatory of the United States of America*, Elaterium, (1918).
*The Merck Manual of Therapeutics and Materia Medica*, Seventh Edition, p. 1365, Merck & Co., Inc., Rahway, N.J. (1940).

* cited by examiner

*Primary Examiner*—Patricia Leith
(74) *Attorney, Agent, or Firm*—Robert P. Michal; Frishauf, Holtz, Goodman & Chick, P.C.

(57) ABSTRACT

An herbal-based treatment for Hepatitis C includes boiling a filtered residue from the Ecballium Elaterium plant to form a condensate. This condensate is mixed with water and administered in the form of drops. The drops were given to human patients, along with a single herb, Camelthorn, in a powder form. The combined herbal-based treatment was administered to human beings who were chronically infected with Hepatitis C. These patients, in terms of reduction of viral loads, normalization of enzymes, and general well being, were treated successfully in most instances.

8 Claims, No Drawings

METHOD FOR TREATING HEPATITIS C WITH EVAPORATE OF *ECBALLIUM ELATERIUM* EXTRACT

CROSS-REFERENCE TO RELATED APPLICATION

This application claims the benefit under 35 USC 119(e) of Provisional application Ser. No. 60/402,373 filed on Aug. 9, 2002.

BACKGROUND OF INVENTION

Hepatitis is a disease of the liver, which is usually caused by viral infections. A significant number of patients suffering from hepatitis are infected with either hepatitis B virus (HBV) or hepatitis C virus (HCV). HCV is an RNA virus with a virion size of 30-60 nm. HBV is a DNA virus with a virion size of 42 nm (D. S. Chen, J. Formos. Med. Assoc., 95(1):6-12 (1996)). Serious complications of hepatitis can include cirrhosis, hepatic failure, liver cancer and death.

As of 1997, nearly 14 million people in the United States and 100 million worldwide were infected with the hepatitis C virus (Alter, M. J., Hepatology, 26(1):625-655 (1997)). It is expected that worldwide, the number of patients has increased to 170 million people in 2002 (ViroPharma Inc. Press Release, Jun. 19, 2002).

Chronic hepatitis C is the most common cause of chronic liver disease and is the leading indication for liver transplantation in the United States (Detre, et al., Viral Hepatitis Rev., 2:219-228 (1996)).

In Egypt, HCV represents the highest donor infection rates recorded so far where 14-24% of blood donors are anti-HCV positive (Hipps, et al., Infect. Dis. 168:789-790 (1993)).

Hepatitis B is a major health problem worldwide, particularly in Asia and Africa. Approximately 300 million people are chronically infected with HBV worldwide and more than one million carriers of HBV are found in the United States. HBV carriers not only become long-term reservoirs of the virus, but also may develop chronic liver disease and have a greatly increased risk of developing liver cirrhosis and cancer.

Unfortunately, there are few effective treatments for hepatitis. Treatment of HCV with recombinant-alpha interferon has a limited long-term efficacy with a response rate of only about 25% (D. S. Chen, J. Formos. Med. Assoc., 95(1):6-12 (1996)). A long-term relapse rate of 24% was reported in Chinese patients with chronic hepatitis B who underwent interferon therapy (Lok, et al., Gastroenterology, 105(6): 1833-1838 (1993)). Furthermore, interferon is associated with a number of adverse side effects, including thrombocytopenia, leucopenia, bacterial infections, and influenza-like symptoms. Other agents used in the treatment of hepatitis include the nucleoside analog ribavirin and ursodeoxycholic acid. However, neither has been shown to be particularly effective (D. C. Dale and D. D. Federman, eds. Medicine Sc. Amer., Inc., New York, 4(8):1-8 (1995)). The most effective treatment now in wide spread use may be the combination of Interferon and Ribavirin. (McHutchison et at New England Journal of Medicine, Vol 339, pps. 1485-1491.

The use of herbal therapy and folk medicines has been known for thousands of years in China. In fact, records on the use of herbs date back to biblical times. However, only recently have scientists begun exploring the possible role for herbs in treatment of viral infections. For example, extracts of *Hemidesmus indicus* rhizomes (Family: Asclepiadaceae) have been found to have anti-viral activity against DNA and RNA viruses (Babbar, et al., Ind. J. Exp. Biol., 8:304-312 (1970)). Likewise, extracts from the root of the Ecballium Elaterium have been used to treat HCV and HBV (EP 0793964 and U.S. Pat. No. 5,648,089). While research in the field of herbal medicines has increased, much remains to be learned about the effectiveness of such herbal remedies.

In view of the above, there is a continuing need in the art for alternative options for treating viral infections such as HCV and HBV. Moreover, there is a need in the art for treatment options that provide minimal side effects.

Accordingly, it is an object of the present invention to provide herbal compositions and methods for treating viral infections such as HCV and HBV. Moreover, it is object of the present invention to provide compositions and methods for treatment that incur minimal side effects to the subject. Another object of the invention is to develop a treatment, which involves a minimum of only two herbal elements. This last object is of vital importance to the eventual large-scale commercial use of a herbal treatment. Current United States regulations impose strict manufacturing controls on the manufacture if pharmaceutical products. Herbal treatments based upon too many herbal component compound manufacturing processes and may make these more complicated treatments commercially impracticable.

The inventors have previously developed a treatment for both Hepatitis C and Hepatitis B, along with other virus caused diseases. The prior attempts involved many different herbs. Some were thought to be anti-viral and some had the purpose of reducing or eliminating side effects. Each treatment had at least ten herbs or extracts from herbs. After a study of United States Federal Drug Administration proposed regulations, the inventors sought to come up with a treatment in which only one or two herbs or extracts from herbs would be used.

One of the extracts was from the herb, Ecballium Elaterium. This herb had long been used to treat liver disease such as jaundice. (See, "Medicinal Plants of North Africa", Loutfy Boulos, Reference Publications, Inc 1983) Ecballium Elaterium could not be used directly as it has some serious toxicity problems.

See *A Manual of Materia Medica and Pharmacology* by David M. R. Culbreth, Ph. G., M.D. (1927) which describes the properties of Ecbalium Elaterium as follows: "PROPERTIES—Hydragogue cathartic (most powerful known), producing profuse watery evacuations with griping and much prostration; large doses nauseate, vomit, inflame stomach and bowels, increase flow of urine, and may kill. Does neither vomit nor purge dogs, rabbits, but kills them by convulsions. Those working in it often have ulcerated fingers, eyes, etc".

Initially the inventors obtained an extract of Ecbalium elaterium preparing herbal drops made by using the fruit of Ecbalium elaterium and washing the fruit with clean water. Approximately a half-kilogram of fruit and one liter of distilled water were combined in an ordinary household electrical grinder. The fruit was ground for two minutes. The mixture was then poured through a sieve of cotton gauze to separate out the larger fruit particles. The mixture was then filtered using Wattmann filter paper. The filtrate (i.e., cell sap) was stored in a refrigerator at 10° C. for approximately 5-7 hours to promote the precipitation of microparticles. The filtrate was then filtered using ceramic sterilization candles to remove any microorganisms. The pH was adjusted to approximately 6.8-7 using dilute sulfuric acid and sodium bicarbonate. A preservative (thiomersal) was added to the sterilized filtrate to provide a concentration of 0.001 gm/liter. The herbal solution was then placed into 10 cc. dropper bottles under aseptic conditions and stored in the refrigerator at about 4 degrees C. The final concentration of the extract was approximately 0.5 weight % cell sap based on the amount of cell sap dissolved in water (5 gms/1000 ml).

This method did produce a successful anti-viral but those treated with Ecbalium elaterium did require additional herbs to minimize side effects. As a result, the treatment had too many herbs, making its future manufacture unfeasible.

The inventors noticed that after placing aluminum foil over the Ecbalium elaterium mixture (in order to protect it from dust) a brown residue would form on the foil. They then isolated the residue and reduced it to liquid form so as to be administered in drops. The inventors surmised that the Ecbalium evaporate might contain an anti-viral and additionally might not contain the toxic part of Ecbalium elaterium. They thought that the evaporate was present at 40 degrees C., as this was roughly the summer temperature in which the Ecbalium elaterium was stored and the discoloring of the covering aluminum occurred. After discarding the use of water, methyl alcohol, and ethyl alcohol, the inventors tried methylene chloride. Methylene chloride is not soluble in water, has mild polarity, and boiling point of 30 to 32 degrees C.

The inventors add the same volume of the solvent, methylene chloride, and the yield-differentiated distillation (using tap water and fresh Ecbalium fruit), then hand shaking for about five minutes in a separating funnel, then leaving the mixture for 30 minutes. This last step gives the solvent a chance for the solvent to be separated form the water due to the different densities. The solvent, which contained the Ecbalium elaterium residue, is then transferred to a rotary evaporation machine. The machine evaporates the solvent away at 29 to 30 degrees C., under vacuum. This process yields about a half milliliter of residue over a period of 3 to 4 hours. The residue is a strong smelling brown oily substance.

A HPLC machine analyzed the above final residue. The result was the largest indication of absorption at 8.648 AU (Angstrom) but the substance remains chemically unidentified. The mechanism of action may be similar to that found by others in extract from Aloe Vera. (See U.S. Pat. No. 5,118,673 Carpenter, et al. Jun. 2, 1992 Uses of aloe products)

The inventors, using their wide experience in herbal therapy, surmised that the herb Camel thorn (Alhagi pseudalhagi), with its long record of versatility, would be a good candidate to test as an anti-viral. Their trial dose of Camel thorn (Alhagi pseudalhagi) in powder form was one teaspoon-full twice a day before meals. They subsequently prepared the single herb in the form of drops by steam distillation process by boiling 0.5 kg of cleaned shoots in 2 liter of tap water thereby gaining 500 ml of a mixture of distilled water and vapor materials. Then, the drops are packed into 10-ml plastic vials. The dose of single herb Camel thorn (Alhagi pseudalhagi) drops is 4 drops nasally once a day.

Since it was known that a combination of ingredients can be more effective in treating Hepatitis C (see Interferon Alfa-2b Alone or in combination with Ribavirin as Initial Treatment for Chronic Hepatitis C, McHutchison et al, New England Journal of Medicine, Vol 339, p 1485-1491, Nov. 19, 1998), the inventors tested both the herbs Alhagi pseudalhagi and Ecballium elaterium residue both singly and in combination.

SUMMARY OF THE INVENTION

The present invention provides three herbal compositions having anti-viral properties and methods of treating viral infections. These are:
1. An extract of Ecballium elaterium (squirting cucumber) prepared in a unique manner.
2. A single herb, Alhagi pseudalhagi (camel thorn).
3. An extract of Ecballium elaterium, prepared in a unique manner, and a single herb, Alhagi pseudalhagi.

The present invention also provides a method for treating a viral infection, which includes administering to a subject an effective amount of either of the three above herbal compositions being selected from among the herbal compositions of the invention. The subjects to be treated are preferably subjects in need of treatment (suffering from a viral infection). Subjects to be treated are preferably mammals in particular humans. Viral infections to be treated include hepatitis C, hepatitis B or a combination of the two and other viral infections such as influenza, viral diabetes, and common cold.

Advantageously, the herbal compositions and methods of the present invention provide an alternative treatment option for subjects suffering from viral infections. In addition, the herbal compositions and methods of the present invention provide an alternative treatment option that exhibits minimal side effects. These and other advantages of the present invention will become readily apparent from the detailed description set forth below.

In the context of the invention, "treating" or "treatment" at a minimum refers to inhibiting the progression of the viral infection, which can be ascertained qualitatively (e.g., by a reduction in clinical symptoms) or quantitatively (e.g., by a reduction in viral load or other quantifiable criteria.). An "effective" amount is any amount of the herbal composition that inhibits or stops the progression of the viral infection. However, as will be apparent to those skilled in the art, the efficacy of a particular composition on a subject will be affected by a variety of factors including, but not limited to, the method of administration, the body mass and age of the subject, and the stage of the infection (e.g., acute or chronic).

As previously described, the herbal compositions of the present invention are particularly suitable for treating a subject having a viral infection. Viruses to be treated include DNA and RNA virus, with hepatitis B virus (HBV) and the hepatitis C virus (HCV) being particularly preferred. In the treatment of HBV or HCV, inhibition of infection can be qualitatively ascertained by determining the presence or absence of the viral genome by polymerase chain reaction (PCR) and reverse transcriptase polymerase chain reaction (RT-PCR), or by observing a reduction and/or disappearance in clinical symptoms such as jaundice, weakness, right hypochondrial pain, loss of appetite, and other symptoms that are associated with hepatitis infection. Efficacy in treating of HBV or HCV can also be quantitatively ascertained by measuring a reduction in viral load using PCR and RT-PCR or by measuring a reduction (i.e., normalization) in elevated liver enzyme levels (e.g., serum alanine transaminase (ALT) and serum aspartate transaminase (AST)). Alternatively, assays for surface antigens of HBV (e.g., HBsAg) and HCV can also be used.

Subjects to whom the herbal compositions of the invention are administered include any living organism, with mammals such as primates and humans being more preferred. The subject is also preferably in need of treatment (i.e., has a viral infection that requires treatment). Accordingly, in a more preferred embodiment, the subject is infected with HBV, HCV or both.

The herbal compositions are administered to the subject by any technique known in the art. Routes of delivery can include, but are not limited to, oral, intranasal, sublingual, intrapulmonary, rectal, transdermal, parenteral and combinations thereof. Acceptable dosage forms suitable for administration to a subject include, but are not limited to, tablets, capsules, powders, patches, solutions, and suspensions. The compositions of the invention can include a physiologically-acceptable carrier in which the herbal extracts are dispersed. For example, the carrier can be buffered saline if a liquid dosage unit is to be prepared. Procedures for making and administering such dosage forms are well within the abilities of one of ordinary skill in the art.

In one particular embodiment, the subject is administered an effective amount of the compositions of the invention, The combined use of these two herbal compositions have been found to be particularly effective in treating subjects infected with HBV and HCV, as compared to using the compositions alone.

DETAILED DESCRIPTION OF THE INVENTION

In accordance with the present invention there are provided herbal compositions useful for the treatment of viral infections, such as hepatitis, and methods of using these compositions. The herbal compositions of the invention are particularly useful for the treatment of hepatitis B and hepatitis C.

Subjects to whom the herbal compositions of the invention are administered include any living organism, with mammals such as primates and humans being more preferred. The subject is also preferably in need of treatment (i.e., has a viral infection that requires treatment). Accordingly, in a more preferred embodiment, the subject is infected with HBV, HCV or both.

The herbal compositions are administered to the subject by any technique known in the art. Routes of delivery can include, but are not limited to, oral, intranasal, sublingual, intrapulmonary, rectal, transdermal, parenteral and combinations thereof. Acceptable dosage forms suitable for administration to a subject include, but are not limited to, tablets, capsules, powders, patches, solutions, and suspensions. The compositions of the invention can include a physiologically-acceptable carrier in which the herbal extracts are dispersed. For example, the carrier can be buffered saline if a liquid dosage unit is to be prepared. Procedures for making and administering such dosage forms are well within the abilities of one of ordinary skill in the art.

In one particular embodiment, the subject is administered an effective amount of the compositions of the invention, with the two-component herbal composition being preferred as the primary herbal composition. The primary herbal composition is preferably administered in liquid form and in a dosage of 2 drops, two times per day. A secondary herbal composition, the Ecbalium elaterium residue only is additionally administered to the subject orally in a dosage of two drops, two times a day. In another embodiment, the liquid drops or powder consisting only of Camel thorn (Alhagi pseudalhagi) are administered either liquid, 2 drops twice a day, or powder, one to five grams, three times a day, with 1 to 3 grams, three times a day being preferred. The combined use of these two herbal compositions have been found to be particularly effective in treating subjects infected with HBV and HCV, as compared to using the compositions alone.

Extracts of the various herbs are prepared following conventional techniques known in the art. The extracts can be prepared as a powdered extract using a maceration extraction process or as a liquid extract using a solvent extraction process. For example, the herbal compositions may be prepared as herbal extracts as taught in U.S. Pat. No. 5,876,728, or in U.S. Pat. No. 5,874,804

The herbal compositions are not limited to any one particular dosage form. The compositions of this invention can be prepared in a variety of dosage forms known in the art. However, as will be apparent to those skilled in the art, the particular dosage form used will be dependent on the delivery route. The herbal compositions can also include excipients to alter taste, bulk, and texture, and can include preservatives to increase shelf life.

In accordance with the present invention, methods of treating viral infections with the herbal compositions of the invention are also provided. The methods entail administering to the subject an effective amount of a primary herbal composition, which includes:

HCV Study

To determine the efficacy of the herbal compositions of the invention, an open 18-month study was conducted with 23 patients infected with the hepatitis C virus. The study involved a treatment regimen using the herbal compositions of the three herbal compositions described above.

Criteria for entry into the study were as follows: (a) testing serum-positive for HCV antibodies within the last 6 months before entry to the study; (b) testing serum-positive for HCV-RNA by RT-PCR within the last 3 months before entry to the study; (c) exhibiting elevated levels of serum alanine transaminase (ALT) and serum aspartate transaminase (AST) within the last 6 months before entry into the study; (d) exhibiting ALT levels at least twice the upper normal level within the last 6 months before entry into the study which at no time during this time period dropped to or below the normal level, and (e) tested again for HCV-RNA by RT-PCR. Patients were excluded from the study if they had another major illness such as major active infections, cancer, or renal failure; evidence of liver disease other than viral hepatitis; or a known history or presence of ascites, hepatomegaly or liver cirrhosis. Patients were also excluded if they were alcoholic or a drug abuser, concurrently used other herbs or folk medicine, concurrently used other antiviral medication, or demonstrated other unsuitable characteristics including severe allergies or dizziness. Dizziness was considered as a criterion for excluding patients because it occurred occasionally after taking the herbal compositions.

RT-PCR of serum was done following conventional techniques using a Sorine kit. RT-PCR was followed by thirty-five (35) cycles of amplification of HCV cDNA. A Triple test (El-Awady, et al., Chem. Clinical Acta, 283(1-2):1-14 (1999)) was also conducted for some patients to assay HCV-RNA in serum and leucocytes (both positive and negative strands). In accordance with this test, negative and positive controls were run with each assay to avoid false negatives and false positives. In addition, as part of the Triple test, subjects were tested for serum viraemia, mature viral genome in peripheral mononuclear cell lysate as well as replicating forms of virus in peripheral leucocytes. This gave an impression of the extra hepatic tissue, in which the absence of replicating forms in extra hepatic tissue after treatment provided a good prognosis of the effectiveness of the herbal compositions. Other PCR tests such b-DNA and AMP were used as well.

The serum AST and ALT levels were assayed following known techniques (Bergmeyer and Horder, Clin. Chen. Acta 105147 f. (1980); International Federation of Clinical Chemistry, Scientific Committee, J. Clin. Chem. Biochem., 18:521-534 (1980); Bergmeyer H. U. Principles of Enzymatic Analysis. Verlag Chemic, (1978)). Assay kits manufactured by Stanbio Laboratories, Inc., (USA), Bio. Merieux (France), and Boehringer Mannheim (Germany) were used.

The patients were divided into 3 groups. The first group (Group A) received the single herb, Alhagi pseudalhagi. The second group (Group B) received herbal drops of the Ecaballium elaterium residue. The third group (Group C) received the single herb Alhagi pseudalhagi and the herbal drops made from the Ecaballium Elaterium residue. (Table 1.)

The health status of each patient was monitored monthly, which included monitoring changes in body weight, blood pressure, eating habits, sleeping habits, strength, pain, and overall appearance. Serum AST and ALT levels were also monitored monthly in addition to other enzyme levels. Following generally accepted practices, normalization of AST and ALT levels was considered to occur when levels fell below twice the normal limits.

Generally, RT-PCR of patients' serum was additionally performed after 6 months of treatment. (Table 2.)

The percentage of patients having normal enzyme levels (i.e., less than twice the normal limit) at the beginning of treatment and during the first 4 months of treatment is listed in Table 3. After 4 months, the number of patients that returned for monthly assessment of enzyme levels began to significantly decrease,

TABLE 1

| Grouping of Patients | Treatment |
| --- | --- |
| Group A | Single herb |
| Group B | Herbal drops |
| Group C | Single herb + herbal drops |

TABLE 2

PCR readings for each patient after treatment

| Group | Patients | High | Moderate | Weak | Negative |
| --- | --- | --- | --- | --- | --- |
| A | 4 | 1 | 3 | 0 | 0 |
| B | 12 | 2 | 4 | 3 | 3 |
| C | 23 | 1 | 4 | 8 | 7 |

TABLE 3

Enzyme readings for each patient after treatment

| Group | Patients | SPGT Normalized | Levels Elevated |
| --- | --- | --- | --- |
| A | 4 | 3 | 1 |
| B | 12 | 12 | 0 |
| C | 23 | 18 | 5 |

Furthermore, all patients in all Groups reported an improvement in symptoms associated with hepatitis such as:
1. Increase in strength sufficient to allow patient work efficiently;
2. Disappearance of right hypochondrial pain and so the patient can sleep on his right side;
3. An improvement of prothrombine synthesis and a corresponding decrease in bleeding;
4. Healing of skin lesions, disappearance of tenderness of skin and soft tissues, and clearance of skin pigmentations in hepatic patients;
5. Improvement of appetite and digestion;
6. Loss of constipation and correction of bowel habits;
7. Disappearance of an earthy look of the face;
8. Decrease attacks of cholecystitis; and
9. Weight gain.

We claim:

1. A method for treating hepatitis C which comprises administering to a subject in need thereof a pharmaceutically effective amount of a composition comprising an agent which is prepared by a method comprising extracting fruit of Ecballium Elaterium with water, allowing the extract to evaporate and collecting a resultant brown evaporate residue, wherein said brown evaporate residue is said agent.

2. The method according to claim 1, wherein the subject is a mammal.

3. The method according to claim 1, wherein the mammal is a human.

4. The method according to claim 3, wherein the composition consists essentially of the agent.

5. The method according to claim 3, wherein the composition consists of the agent.

6. A method for treating hepatitis C which comprises administering to a subject in need thereof a pharmaceutically effective amount of a combination of (i) an agent which is prepared by a method comprising extracting fruit of Ecballium Elaterium with water, allowing the extract to evaporate and collecting a resultant brown evaporate residue, wherein said brown evaporate residue is said agent and (ii) *Alhagi pseudalhagi*.

7. The method according to claim 6, wherein the subject is a mammal.

8. The method according to claim 6, wherein the subject is a human.

* * * * *